(12) United States Patent
Helfenbein et al.

(10) Patent No.: US 9,604,069 B2
(45) Date of Patent: Mar. 28, 2017

(54) DEFIBRILLATOR AND METHOD USING LIMB LEADS FOR ARTIFACT FREE ECG

(71) Applicant: KONINKLIJKE PHILIPS N.V., Eindhoven (NL)

(72) Inventors: Eric Helfenbein, Sunnyvale, CA (US); Saeed Babaeizadeh, Arlington, MA (US); Sophia Huai Zhou, Briarcliff Manor, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/774,969

(22) PCT Filed: Mar. 11, 2014

(86) PCT No.: PCT/IB2014/059614
§ 371 (c)(1),
(2) Date: Sep. 11, 2015

(87) PCT Pub. No.: WO2014/141056
PCT Pub. Date: Sep. 18, 2014

(65) Prior Publication Data
US 2016/0015990 A1  Jan. 21, 2016

Related U.S. Application Data

(60) Provisional application No. 61/777,160, filed on Mar. 12, 2013.

(51) Int. Cl.
*A61B 5/04* (2006.01)
*A61N 1/39* (2006.01)
(Continued)

(52) U.S. Cl.
CPC ............ *A61N 1/3925* (2013.01); *A61B 5/044* (2013.01); *A61B 5/04085* (2013.01);
(Continued)

(58) Field of Classification Search
CPC ... A61B 5/04085; A61B 5/044; A61B 5/7207; A61N 1/046; A61N 1/39; A61N 1/3925; A61N 1/3993
See application file for complete search history.

(56) References Cited

U.S. PATENT DOCUMENTS 5,902,249 A   5/1999   Lyster
6,021,349 A   2/2000   Arand et al.
(Continued)

FOREIGN PATENT DOCUMENTS

WO   2014141080 A1   9/2014

OTHER PUBLICATIONS

ZOLL Advancing Resuscitation, Today. Rseries Operator's Guide. Dec. 2007.
12-Lead ECG Monitoring. ZOLL Mseries. (2002).

*Primary Examiner* — George Manuel

(57) ABSTRACT

A defibrillator and method that uses ECG signals from limb lead electrodes for display and monitoring, even when a separate set of therapy pads are present at the patient. The limb lead ECG signal is used for display and to determine whether electrotherapy is necessary. The determination is a prerequisite to arming and delivery of the electrotherapy.

15 Claims, 9 Drawing Sheets

(51) Int. Cl.
    *A61B 5/0408*     (2006.01)
    *A61B 5/044*     (2006.01)
    *A61B 5/00*     (2006.01)
    *A61N 1/04*     (2006.01)

(52) U.S. Cl.
    CPC ............ *A61B 5/7207* (2013.01); *A61N 1/046* (2013.01); *A61N 1/39* (2013.01); *A61N 1/3993* (2013.01)

(56) References Cited

U.S. PATENT DOCUMENTS

| | | | | |
|---|---|---|---|---|
| 6,148,233 | A * | 11/2000 | Owen | A61N 1/0452 607/5 |
| 7,818,049 | B2 | 10/2010 | Halperin et al. | |
| 7,957,799 | B2 | 6/2011 | Sullivan et al. | |
| 8,315,693 | B2 | 11/2012 | Lu et al. | |
| 8,509,881 | B2 | 8/2013 | Thiagarajan et al. | |
| 2008/0027338 | A1 * | 1/2008 | Lu | A61B 5/0424 600/509 |

* cited by examiner

DEFIBRILLATOR AND METHOD USING LIMB LEADS FOR ARTIFACT FREE ECG

This application is a national stage application under 35 U.S.C. §371 of International Application No. PCT/IB2014/059614 filed on Mar. 11, 2014 and published in the English language on Sep. 18, 2014 as International Publication No. WO/2014/141056, which claims priority to U.S. Application No. 61/777,160 filed on Mar. 12, 2013, the entire disclosures of which are incorporated herein by reference.

The invention relates generally to an improved method, apparatus and system for monitoring a subject cardiac rhythm during the application of cardio-pulmonary resuscitation (CPR). More particularly, the invention relates to a medical device which can automatically select one set from a plurality of sets of electrocardiogram (ECG) electrodes having reduced CPR noise artifact for display and for use in determining whether an electrotherapy shock is indicated. If the device is a defibrillator, the method can control the device electrotherapy circuit based on a shock advisory obtained from the lower noise electrode set.

Sudden cardiac arrest (SCA) is a leading cause of death in the United States. In about 40% of sudden cardiac arrest (SCA) patients, the initial cardiac rhythm observed is ventricular fibrillation (VF). CPR is the protocol treatment for SCA, which includes chest compressions and ventilations that provide circulation in the patient. Defibrillation is interposed between sessions of CPR in order to treat underlying VF.

Defibrillators deliver a high-voltage impulse to the heart in order to restore normal rhythm and contractile function in patients who are experiencing arrhythmia, such as VF or ventricular tachycardia (VT) that is not accompanied by spontaneous circulation. There are several classes of defibrillators, including manual defibrillators, implantable defibrillators, and automatic external defibrillators (AEDs). AEDs differ from manual defibrillators in that AEDs can automatically analyze the ECG rhythm to determine if defibrillation is necessary.

FIG. 1 is an illustration of a defibrillator 10 being applied by a user 12 to resuscitate a patient 14 suffering from cardiac arrest. In sudden cardiac arrest, the patient is stricken with a life threatening interruption to the normal heart rhythm, typically in the form of VF or VT that is not accompanied by spontaneous circulation (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient will likely die. Conversely, the quicker that circulation can be restored (via CPR and defibrillation) after the onset of VF, the better the chances that the patient 14 will survive the event. The defibrillator 10 may be in the form of an AED capable of being used by a first responder. The defibrillator 10 may also be in the form of a manual defibrillator for use by paramedics or other highly trained medical personnel.

According to an exemplary embodiment of the present disclosure, electrotherapy electrodes 16 are applied across the chest of the patient 14 by the user 12 in order to provide defibrillation shocks. The same electrotherapy electrodes 16 can also acquire an ECG signal from the patient's heart. The defibrillator 10 then analyzes the ECG signal for signs of arrhythmia. If VF is detected, the defibrillator 10 signals the user 12 that a shock is advised. After detecting VF or other shockable rhythm, the user 12 then presses a shock button on the defibrillator 10 to deliver defibrillation pulse to resuscitate the patient 14. Defibrillator 10 can also display the ECG from the therapy electrodes 16 on a screen, so that the user 12 can manually assess the underlying cardiac rhythm. Currently available AED devices can typically receive ECG input only from such electrotherapy electrodes 16.

More advanced defibrillators, exemplified also by defibrillator 10 of FIG. 1, may also provide for a second set of monitoring electrodes 18 to be applied to standard positions on the patient torso and limbs. Monitoring electrodes 18 cannot be used to deliver electrotherapy, and are usually used to provide prolonged and more accurate ECG signals obtained from various heart axes, or leads. These ECG signals may also be displayed on defibrillator 10 screen.

Existing advanced defibrillators may be capable of receiving input from both therapy electrodes and monitoring electrodes simultaneously. In such case, however, all such defibrillators default to display the therapy electrodes ECG. And all such prior art defibrillators are known to use strictly the therapy electrode—derived ECG for analysis, regardless of whether monitoring electrodes are attached.

FIG. 2 illustrates the common standard electrode positions relative to an adult patient for defibrillation and for cardiac monitoring. Sternum therapy pad 22 is generally applied over the patient 14 right clavicle. Apex therapy pad 24 is applied on the patient's lower left torso, such that a defibrillation current path passes through the patient's heart. Standard ECG monitoring electrodes include right arm (RA) limb lead 32', left arm (LA) limb lead 32", left leg (LL) limb lead 32''', and right leg (RL) limb lead 32'''' placed on the patient's extremities and/or lower torso as indicated. Chest lead monitoring electrodes 34 are typically arranged nearer and over the heart location. A common standard location for providing manual CPR compressions is shown as region 26. It can be seen from FIG. 2 that the CPR region 26 lies at or about mid-way along the axis between sternum electrode 22 and apex electrode 24, the axis generally correlating to the standard Lead II axis.

Chest compressions during CPR tend to create signal artifact on the ECG waveforms that are acquired from therapy defibrillation pads on the chest. The CPR artifact on the ECG waveform generally comes from four main sources. First, artifact arises from a change in impedance due to changes in electrode-skin contact. Second, stretching of the skin which tends to occur during CPR induces electrical potentials. Also, muscle potentials (EMG) are typically induced by CPR forces that are applied to the chest muscles. Muscle potentials are also typically induced by CPR forces that are indirectly applied to the heart muscle. As previously noted, multifunction ECG/defibrillation therapy pads applied to the patient's chest are in the vicinity of the sternum where CPR compressions are delivered. Because of this proximity, the artifact from the noise sources above can be quite large.

The compression artifact should be filtered out or the compression stopped for the rescuer or an automated shock-advisory algorithm to see the underlying ECG rhythm to determine if a shock should be applied. Otherwise, this artifact tends to mask the underlying ECG rhythm, making it difficult for the rescuer or the automated shock-advisory algorithm to determine if the patient should be given a defibrillation shock.

FIG. 3 shows an exemplary 23-second ECG strip from a sudden cardiac arrest (SCA) patient whose underlying rhythm is VF. The first half 50 of the waveform is recorded during CPR and so shows the CPR artifact signal superimposed over the VF signal. The second half 60 is recorded after CPR has been paused and hence, shows the VF signal without any CPR artifact signal. As seen, during CPR, the chest compression artifact induced on the ECG masks the underlying VF rhythm. A shock advisory algorithm could be fooled by the CPR artifact on the left side 50 to erroneously recommend no-shock advised. For the right side 60, however, since there is no CPR artifact on the ECG, a shock advisory algorithm can accurately detect the VF rhythm and advise shock.

But it has been shown that interruptions in CPR compressions to allow for such artifact-free ECG analysis can be detrimental to the patient. It is now understood that cardiac perfusion pressure drops rapidly during CPR pauses, and that it takes approximately 15 seconds after CPR compressions are resumed before cardiac perfusion pressure returns to therapeutic levels. FIG. 4 illustrates the drop in cardiac perfusion pressure that occurs when CPR is paused, as well as the significant number of compressions required to regain peak pressure after CPR is resumed. The CPR pauses have further been shown to adversely affect the probability of restoration of spontaneous circulation after the delivery of the electrical shock.

A number of methods have been developed in an attempt to determine an accurate ECG measurement during CPR compressions. U.S. Patent Publication 2011/0105930 A1 entitled "TRUE ECG MEASUREMENT DURING CARDIO PULMONARY RESUSCITATION BY ADAPTIVE PIECEWISE STITCHING ALGORITHM", for example, discloses using a filter to remove CPR artifact from the ECG. U.S. Pat. No. 7,818,049 B2 entitled "ECG SIGNAL PROCESSOR AND METHOD" by Halperin et al additionally teaches the use of an input from a handheld CPR force sensor to assist with the filtering artifact from ECG. None of these filtering methods have yet been adopted for use in determining either an automated shock decision or for diagnosing a cardiac condition.

What is needed therefore is an improved apparatus and method for displaying an ECG and for diagnosing a shockable cardiac rhythm in the presence of CPR-induced noise artifact. A solution to the need would allow pauses between CPR and defibrillation to be shorter or even eliminated. An ECG waveform having minimal CPR artifact noise can enable a trained user to quickly diagnose a shockable rhythm, via display, or would make an automated shock advisory algorithm more accurate.

The inventors, having studied the differences between ECG signals from limb leads and ECG signals from defibrillation therapy pads, have learned that ECG from limb lead electrodes, rather than pads, can contain significantly less CPR artifact. Applying this learned knowledge, the inventors have invented a defibrillator and method as described herein that use ECG from limb lead electrodes for display and monitoring of ECG even when therapy pads are present. Exemplary embodiments of the present invention can be useful for both manual and automated shock advisories.

In accordance with the principles of the present invention, exemplary embodiments of device, system and method for selectively displaying an ECG on a defibrillator during a cardiac resuscitation of a subject are described. For example, an exemplary embodiment of the method can comprise the steps of providing a defibrillator having a display, a therapy electrodes connector, a monitoring electrodes connector, a processor operable to obtain an ECG responsive to inputs from either of the therapy electrodes connector and the monitoring electrodes connector, and a controller operable to sense a connection of therapy electrodes to the therapy electrodes connector and operable to sense a connection of monitoring electrodes to the monitoring electrodes connector, displaying an ECG obtained from the therapy electrodes connector, sensing both of the connection of a set of therapy electrodes to the therapy electrodes connector and the connection of a set of monitoring electrodes to the monitoring electrodes connector, and automatically switching the displaying of an ECG obtained from the therapy electrodes connector to a displaying of an ECG obtained from the monitoring electrodes connector responsive to the sensing step. The method may optionally include the toggling of the display back to the therapy electrodes ECG if the ECG is determined to be noise-free.

It is another object of the present invention to describe an improved method for operating a defibrillator during a cardiac resuscitation of a subject, an exemplary embodiment of which can comprise the steps of providing a defibrillator having a therapy electrodes connector, a monitoring electrodes connector, a processor operable to obtain an ECG responsive to inputs from either of the therapy electrodes connector and the monitoring electrodes connector and further operable to analyze the obtained ECG to determine whether electrotherapy is indicated, and a controller operable to sense a connection of therapy electrodes to the therapy electrodes connector and operable to sense a connection of monitoring electrodes to the monitoring electrodes connector, analyzing an ECG obtained from the therapy electrodes connector, sensing the connection of both a set of therapy electrodes to the therapy electrodes connector and the connection of a set of monitoring electrodes to the monitoring electrodes connector, and automatically switching the analyzing of an ECG obtained from the therapy electrodes connector to an analyzing of an ECG obtained from the monitoring electrodes connector responsive to the sensing step. The method may optionally include the toggling of the analyzing back to the therapy electrodes ECG if the ECG is determined to be noise-free.

It is yet another object of the invention to describe a defibrillator which incorporates the improved ECG analysis method described above. For example, an exemplary embodiment of the defibrillator can comprise a therapy electrode connector operable to connect to a set of electrotherapy electrodes, a monitoring electrode connector operable to connect to a set of monitoring electrodes, a processor operable to analyze an ECG obtained from either of the electrotherapy electrodes or the monitoring electrodes and to determine a shock decision based on the obtained ECG, a sensing means operable to sense the connection of the set of monitoring electrodes to the monitoring electrode connector and further operable to automatically select a shock decision based on the ECG obtained from the monitoring electrodes in response to the sensed connection, and a high voltage shock delivery circuit operable to deliver an electrotherapy shock via the therapy electrode connector and electrotherapy electrodes in response to the shock decision based on the ECG obtained from the monitoring electrodes. The sensing means can be hardware logic, software logic, or a combination of the two. For example, the sensing means can comprise one or more sensors and/or controllers. Further, a sensor can comprise a controller. The defibrillator can optionally include an artifact detector for the therapy electrodes input, wherein the sensing means is operable to toggle the shock decision source back to the therapy electrodes ECG if the level of noise artifact is below a predetermined noise level.

It is yet another object of the invention to describe a defibrillator which incorporates the improved ECG display method described above. An exemplary embodiment of the defibrillator can comprise a therapy electrode connector operable to connect to a set of electrotherapy electrodes, a monitoring electrode connector operable to connect to a set of monitoring electrodes, a processor operable to obtain an ECG from either of the electrotherapy electrodes or the monitoring electrodes, a sensing means operable to sense the connection of the set of monitoring electrodes to the monitoring electrode connector and further operable to automatically select the ECG obtained from the monitoring electrodes for display in response to the sensed connection, and a display operable to display the selected ECG. The sensing means can be hardware logic, software logic, or a combination of the two. For example, the sensing means can comprise one or more sensors and/or controllers. Further, a sensor can comprise a controller. The defibrillator can optionally include an artifact detector for the therapy electrodes input, wherein the sensing means is operable to toggle the display back to the therapy electrodes ECG if the level of noise artifact is below a predetermined noise level.

IN THE DRAWINGS

Figure 1:
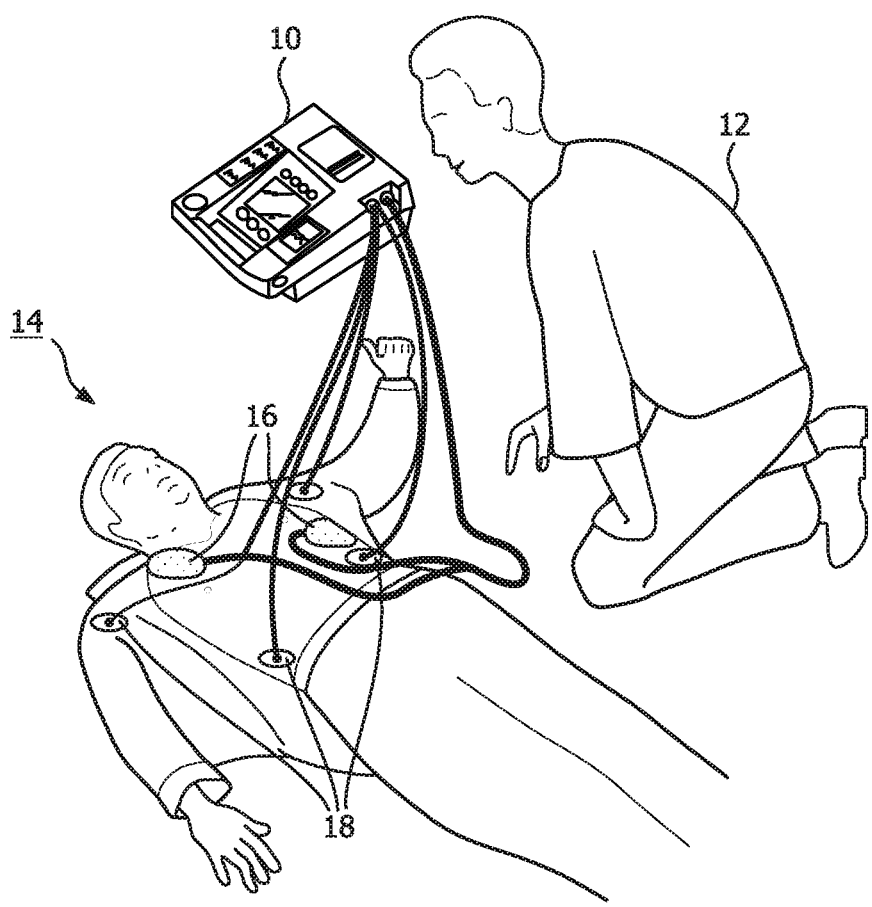
FIG. 1 is an exemplary illustration of a defibrillator which is in use with a patient suffering from cardiac arrest.
Figure 2:
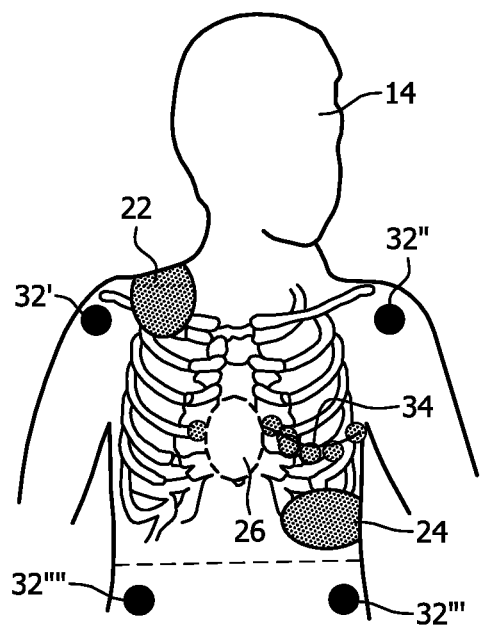
FIG. 2 is an exemplary illustration of common standard electrode positions relative to an adult patient for defibrillation and for cardiac monitoring.
Figure 3:
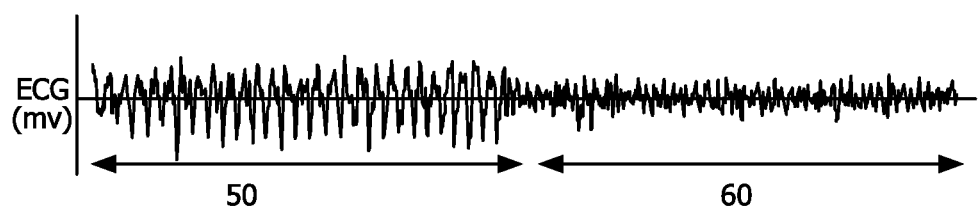
FIG. 3 is an exemplary illustration of a 23-second ECG strip from a sudden cardiac arrest (SCA) patient whose underlying rhythm is VF.
Figure 4:
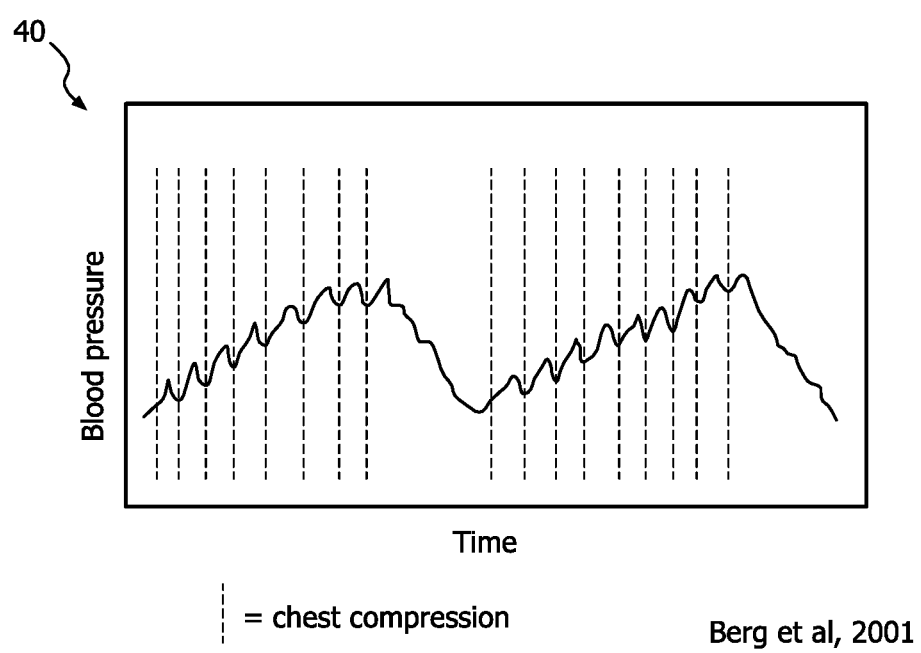
FIG. 4 is an exemplary illustration of the drop in cardiac perfusion pressure that tends to occur when CPR is paused, as well as the significant number of compressions typically required to regain peak pressure after CPR is resumed.
Figure 5:
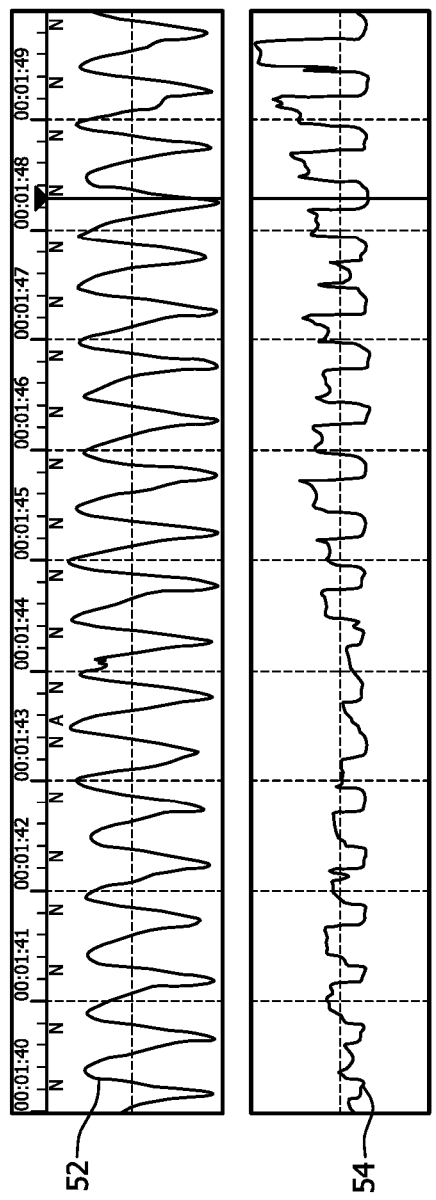
FIG. 5 is an exemplary illustration of CPR-related noise artifact on a patient having no cardiac rhythm, i.e. in asystole, wherein the ECG signal is obtained from the therapy pads.

With further reference to the figures, FIG. 5 illustrates an exemplary 23-second ECG strip from a subject patient with no underlying cardiac rhythm. The top panel indicates an ECG signal obtained from therapy pads during CPR. The ECG trace 52 indicates pure CPR artifact on the therapy pads. The bottom panel shows the impedance between the pads, where each peak corresponds to a CPR compression. Thus the bottom trace 54 indicates pure CPR-induced therapy pad impedance. It can be seen by FIG. 5 the large corresponding oscillations, >20 milliVolts (mV), in the pad ECG which is CPR artifact. The ECG amplitude scale is −16 to 16 mV. The corresponding impedance variation is between +113 milliOhms (mOhm) and 92 mOhm, where the impedance amplitude scale is +113.82 to +83.82 mOhm.

Figure 6:
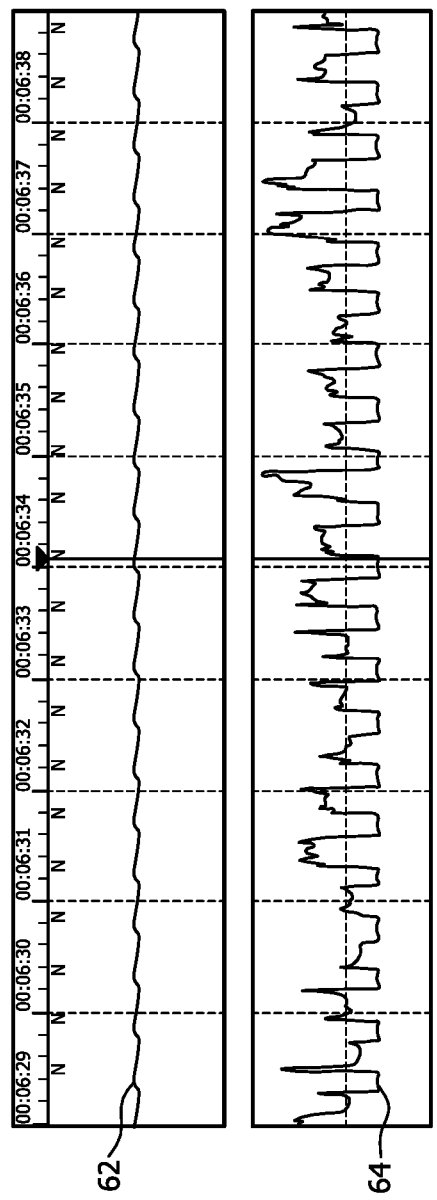
FIG. 6 is an exemplary illustration of CPR-related noise artifact on a patient having no ECG, i.e. in asystole, obtained from the monitoring electrodes.

FIG. 6 illustrates another exemplary 23-second ECG strip from a subject patient with no underlying cardiac rhythm. This top panel indicates an ECG signal obtained from the Lead II monitoring electrodes during CPR. The ECG trace 62 indicates pure CPR artifact on the monitoring electrodes. The bottom panel shows the impedance between the therapy pads, where each peak also corresponds to a CPR compression. Thus the bottom trace 64 indicates pure CPR-induced therapy pad impedance. It can be seen by FIG. 6 the much smaller corresponding oscillations, about 1 mV, in the monitoring electrode ECG which is CPR artifact. The ECG amplitude scale is −16 to 16 mV. The corresponding impedance varies between +198 mOhm and 95 mOhm, where the impedance amplitude scale is +198.232 to +48.232 mOhm One can deduce that the magnitude of pure CPR-induced artifact on the ECG is smaller on the monitoring electrodes than on the therapy pads.

Figure 7:
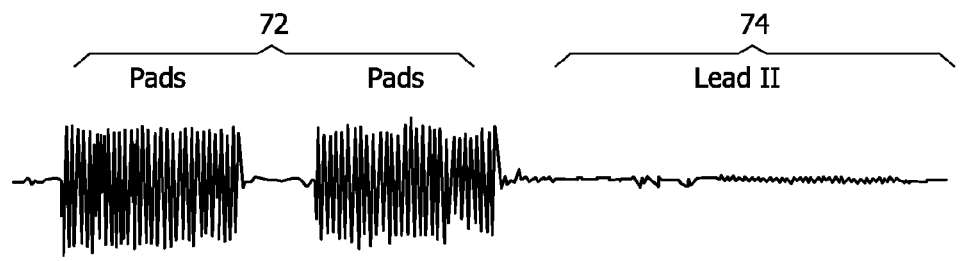
FIG. 7 is an exemplary illustration of a side by side comparison of CPR artifact noise levels for therapy pads and for monitoring electrodes.

FIG. 7 illustrates a side by side comparison of CPR artifact noise levels for therapy pads and for monitoring electrodes, over a longer time frame. The two large sets of oscillations 72 in the first half are the ECG from pads; the smaller oscillations 74 on the right half are from Lead II monitoring electrodes. Here it again can be seen that the magnitude of pure CPR-induced artifact on the ECG is smaller on the monitoring electrodes than on the therapy pads.

Figure 8:
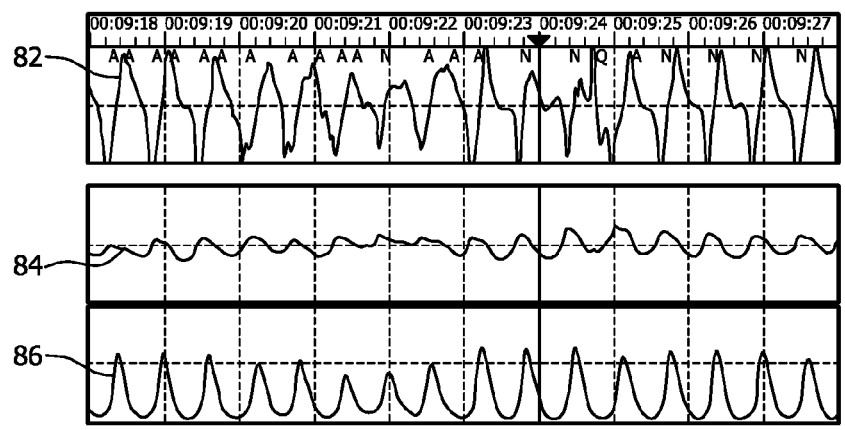
FIG. 8 is an exemplary illustration of CPR-related noise artifact on a patient having no ECG, i.e. in asystole, obtained from the therapy pads, plotted with a chest force signal obtained from a CPR compressions sensor.

FIG. 8 illustrates CPR-related noise artifact on a patient having no ECG, i.e. in asystole, obtained from the therapy pads, plotted with a chest force signal obtained from a CPR compressions sensor, such as from the Q-CPR sensor manufactured by Philips Medical Systems, Andover Mass. The approximately 10-second ECG strip is obtained from a subject patient with no underlying cardiac rhythm. The top panel indicates an ECG signal obtained from therapy pads during CPR. The ECG trace 82 indicates pure CPR artifact on the therapy pads. The center panel shows the impedance between the pads, where each peak corresponds to a CPR compression. Thus the middle trace 84 indicates pure CPR-induced therapy pad impedance. It can be seen by FIG. 8 the large corresponding oscillations, >8 mV, in the pad ECG which is CPR artifact. The ECG amplitude scale is −4 to 4 mV. The corresponding impedance variation is about 6.25 mOhm, where the impedance amplitude scale is +123.3 to +103.3 mOhm. The major oscillations in the ECG correspond to CPR compressions, whose locations are shown by the oscillations in impedance and the chest force sensor trace 86 shown in the bottom panel.

Figure 9:
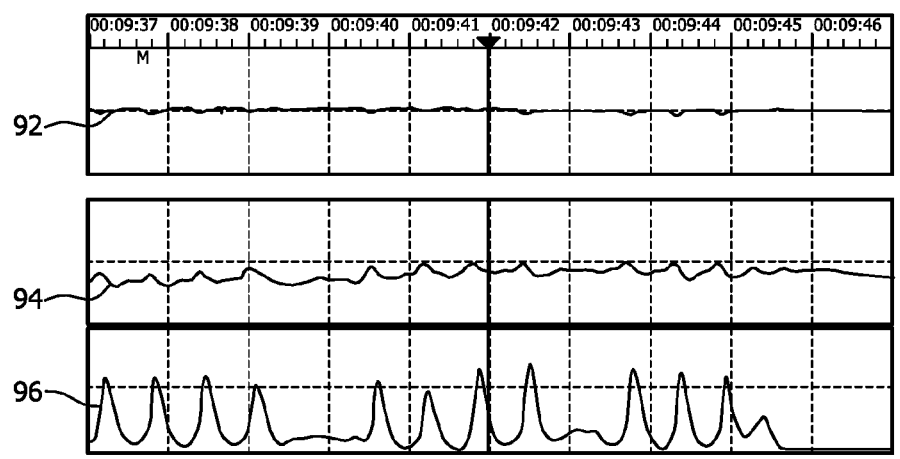
FIG. 9 is an exemplary illustration of CPR-related noise artifact on a patient having no ECG, i.e. in asystole, obtained from the monitoring electrodes, plotted with a chest force signal obtained from a CPR compressions sensor.

FIG. 9 illustrates CPR-related noise artifact on a patient having no ECG, i.e. in asystole, obtained from the monitoring electrodes, plotted with a chest force signal obtained from a CPR compressions sensor. The top panel indicates an ECG signal obtained from monitoring electrodes Lead II during CPR. The ECG trace 92 indicates pure CPR artifact on the monitoring electrodes Lead II. The center panel shows the impedance between the therapy pads, where each peak corresponds to a CPR compression. Thus the middle trace 94 indicates pure CPR-induced therapy pad impedance. It can be seen by FIG. 9 the much smaller corresponding oscillations in the monitoring electrode ECG which is CPR artifact. The ECG amplitude scale is again −4 to 4 mV. The corresponding impedance variation is about 2.5 mOhm, where the impedance amplitude scale is +123.3 to +103.3 mOhm. The minor oscillations in the ECG correspond to CPR compressions, whose locations are shown by the oscillations in impedance and the chest force sensor trace 96 shown in the bottom panel.

Figure 10:
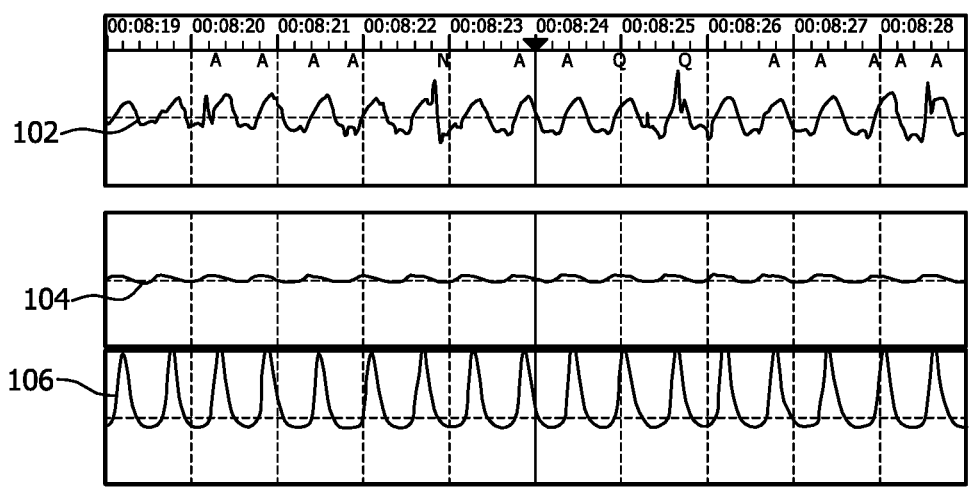
FIG. 10 is an exemplary illustration of CPR-related noise artifact on a patient that has a cardiac rhythm, obtained from the therapy pads, plotted with a chest force signal obtained from a CPR compressions sensor.

FIG. 10 illustrates CPR-related noise artifact as obtained from therapy pads placed on a patient that has a cardiac rhythm. Again, the ECG trace 102 is plotted with a pad-pad impedance signal 104 and a chest force signal 106 obtained from a CPR compressions sensor. The ECG amplitude scale is −2 to 2 mV. The corresponding impedance variation is about 3.1 mOhm, where the impedance amplitude scale is +143.8 to +93.8 mOhm Like in FIG. 8, the major oscillations in the ECG correspond to CPR compressions, whose locations are shown by the oscillations in impedance and chest force. The underlying cardiac rhythm in the ECG is effectively obscured by the CPR artifact.

Figure 11:
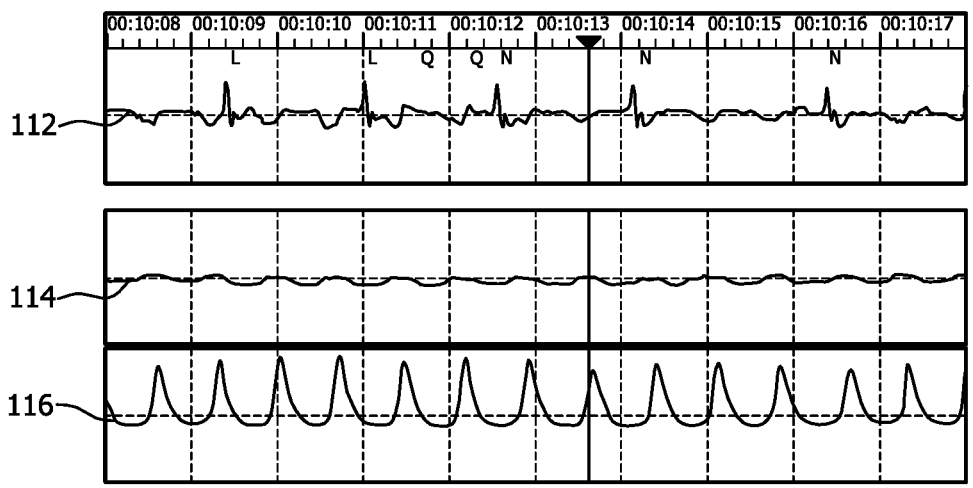
FIG. 11 is an exemplary illustration of CPR-related noise artifact on a patient that has a cardiac rhythm, obtained from the monitoring electrodes, plotted with a chest force signal obtained from a CPR compressions sensor.

In contrast, FIG. 11 illustrates CPR-related noise artifact as obtained from monitoring electrodes at Lead II placed on a patient that has a cardiac rhythm. Similar to that in FIGS. 8-10, the ECG trace 112 is plotted with a therapy pad-pad impedance signal 114 and a chest force signal 116 obtained from a CPR compressions sensor. The ECG amplitude scale is −2 to 2 mV. It is observed here that only minor oscillations in the ECG result from CPR compressions, whose locations are shown by the oscillations in impedance and chest force. The underlying cardiac rhythm is clear in the ECG despite the CPR compressions.

The inventors have learned from the afore-described data that the ECG from relatively small monitoring electrodes placed on the patient's shoulders and lower abdomen generally have less CPR artifact compared to ECG from the relatively larger multifunction therapy pads. It should be noted that the ECG from monitoring electrodes may still contain some residual CPR artifact (as seen in the above figures), and thus may still benefit from additional filtering such as that described in U.S. application No. 61/654,143 entitled "Method and Apparatus for Analyzing Cardiac Rhythm During CPR", filed Jun. 1, 2012, the entire disclosure of which is incorporated herein by reference.

For convenience in this description, the display and use of ECG from limb lead electrodes is referred to as the "LeadView" feature.

An advanced life support (ALS) defibrillator or a basic life support (BLS) AED device may be manufactured with the LeadView option. The defibrillator generally must allow input from both multifunction pads and limb lead electrodes. Current ALS defibrillators have this capability, but it is believed that this would be new capability for an AED device. When both pads and lead electrodes are applied to the patient, priority is given to the ECG from the lead electrodes for both display and input to the shock advisory algorithm.

Figure 12:
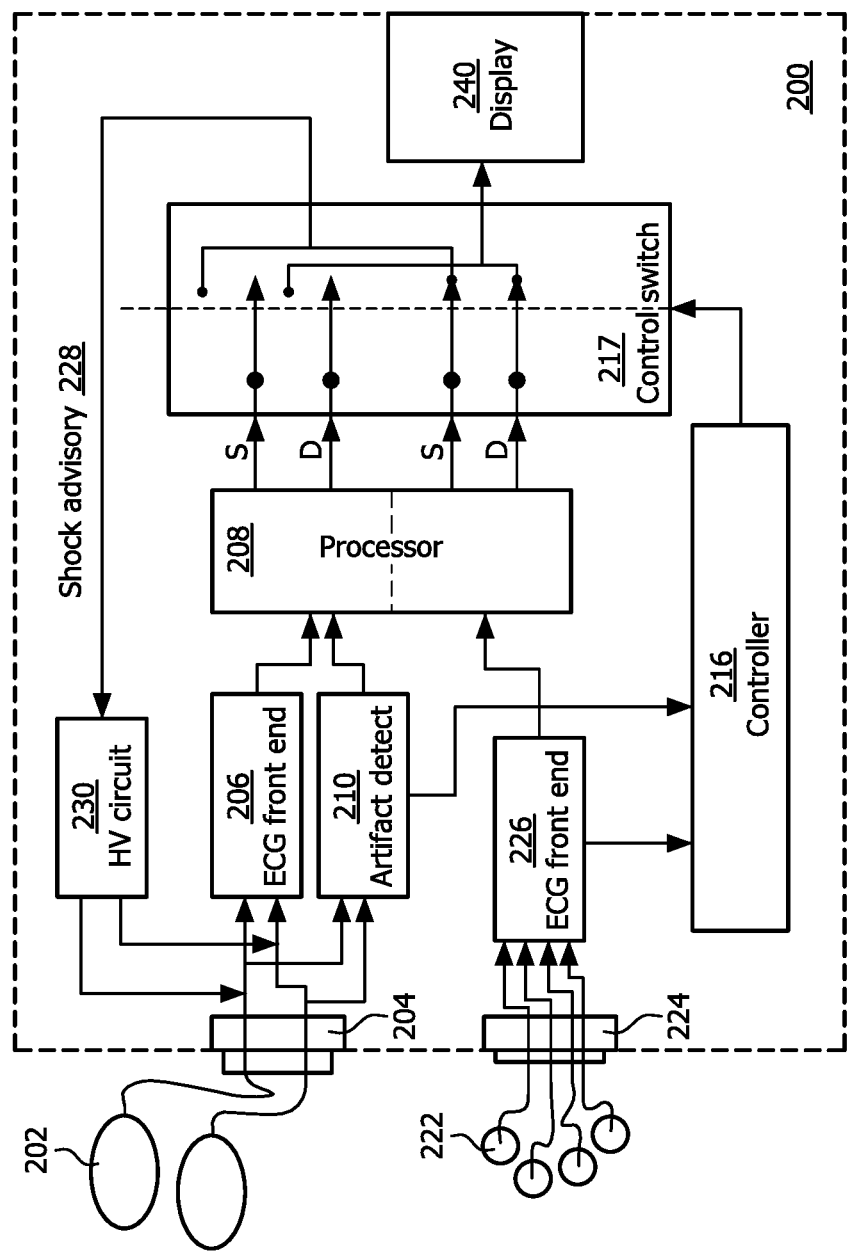
FIG. 12 is an exemplary block diagram of a defibrillator constructed in accordance with the principles of the present invention.

Now turning to FIG. 12, illustrated is a block diagram of an exemplary embodiment of a defibrillator 200 that is constructed in accordance with the principles of the present invention. One embodiment of the defibrillator 200 comprises an ALS defibrillator operating in manual mode, or a BLS AED that is capable of displaying an ECG. When defibrillator 200 senses that both a set of therapy pads 202 and limb lead monitoring electrodes 222 are attached to the patient, defibrillator 200 automatically switches the source of ECG from the therapy pads to the limb lead electrodes for display on a display 240. This can permit the trained rescuer to view the underlying cardiac rhythm having the least CPR noise artifact during continuous chest compressions. Furthermore, if the defibrillator 200 is equipped with a CPR artifact reduction algorithm, the ECG waveforms display 240 may show the ECG from the monitoring electrodes after filtering by that algorithm.

Defibrillator 200 comprises two separate electrode connectors carrying two different ECG data streams. A therapy pads connector 204 operably connects defibrillator 200 to the set of therapy pads 202. Signals from the therapy pads 202 are passed via pads connector 204 to a therapy pads ECG front end 206, which converts the signals into a stream of pads ECG data. The pads ECG data is then provided to processor 208.

Similarly, a monitoring electrodes connector 224 operably connects defibrillator 200 to the limb lead electrodes 222. Preferably, the limb lead electrodes 222 are operable to be disposed on a patient in a standard limb lead orientation. Signals from the limb lead electrodes 222 are passed via electrodes connector 204 to a monitoring electrodes ECG front end 226, which converts the signals into streams of lead electrodes ECG data. The electrodes ECG data is passed to processor 208.

An optional artifact noise detector 210 may be disposed to receive ECG signals from therapy pads 202 in parallel to pads front end 206 in accordance with exemplary embodiments of the present disclosure. The artifact detector 210 can be operable to obtain the level of noise artifact, including CPR-related noise artifact on the ECG obtained from the pads. One such circuit for determining noise artifact is described in co-assigned U.S. Pat. No. 5,902,249 entitled "Method and Apparatus for Detecting Artifacts Using Common-Mode Signals in Differential Signal Detectors" by Thomas J. Lyster, the entire disclosure of which is incorporated herein by reference. Alternatively, the artifact detector 210 may be disposed as described in aforementioned U.S. application No. 61/654,143, the entire disclosure of which is incorporated herein by reference. The output of noise detector 210 may be either a pads noise level, or a determination whether the obtained level of noise artifact is below a predetermined noise level. The determination indicates that CPR is not being performed and/or that the pads ECG is sufficiently noise-free for further use. The noise detector 210 level/decision is provided to processor 208.

Processor 208 can perform several functions on the ECG streams that it obtains from the therapy pads and the monitoring electrodes. For example, first, it arranges the ECG streams into a form appropriate for display. Processor 208 can also perform analysis on each ECG stream to, for example, diagnose a particular cardiac condition, and to provide a corresponding output indication to display 240. In one exemplary embodiment of the present invention, processor 208 can arrange both ECG streams into form for simultaneous display on display 240. Processor 208 can further be disposed to filter the ECG streams prior to display, such that noise artifact is removed or reduced in the displayed ECG. Processor 208 can further use signals from artifact noise detector 210 to filter one or both of the ECG streams. Finally, processor 208 can determine a level of noise artifact for indication on display 240, such as providing a message of "CPR detected" or "noisy ECG, check electrodes", in response to the ECG streams and/or the noise detector 210 input. Preferably, processor 208 provides a display output from each ECG source, signified as "D" in FIG. 12, for further selection and use by the system.

According to exemplary embodiments of the present disclosure, defibrillator 200 further includes a sensing means for sensing when the monitoring electrodes have been attached to a patient, and for selecting the ECG stream from the monitoring electrodes for display in response to the sensed attachment. Several known methods for sensing the patient connection can be used, including sensing a common mode signal between electrode connections at the monitoring electrode connector, sensing an ECG signal at the ECG front end 226, sensing a patient-appropriate impedance between electrodes, all of which can be supplemented with a sensing of the electrode hardware to the monitoring electrodes connector 224 itself. In a preferred embodiment, the sensing means is disposed as a controller 216 and a control switch 217 in a hardware circuit. A functionally equivalent sensing means may also be embodied in software with a microprocessor and memory, or as a software/hardware state machine system.

In a preferred embodiment, controller 216 receives a signal from electrodes ECG front end 226 which indicates that the set of monitoring electrodes 222 is connected to the patient via the monitoring electrodes connector 224. In response to the sensed connection, connector 216 controls controller switch 217 to automatically switch a display source, signified by the "D" inputs from processor 208, to the monitoring electrodes source. The ECG signal from the monitoring electrodes 222 is thus provided to display 240.

Controller 216 can optionally receive input from artifact noise detector 210. If the detected level of noise artifact is below a predetermined noise level, then controller 216 may drive controller switch 217 to toggle the ECG display back to the therapy pads source. This option can be desirable for some users that prefer to display ECG from therapy pads whenever possible and useful, or in situations where the therapy pads ECG display is more accurate or easier to interpret than the monitoring electrodes display, for example.

It will be appreciated by one having ordinary skill in the art in view of teachings provided herein, that the predetermined noise level can be determined by one having ordinary skill in the art in view of the teachings provided herein by conducting a series of trial and error experiments that have varying amounts of known noise and ECG signal levels present. Simulated ECG signal data can be fed into the system under various conditions of noise artifact presence, including CPR-related artifact. This and other methods of finding such heuristic values are well known to those skilled in the art.

It is to be noted that in the absence of the monitoring electrodes, the nominal source of ECG display in defibrillator 200 is the same as that of prior art defibrillators, i.e. the therapy pads 202 ECG. Consequently, controller 216 controls controller switch 217 to route the therapy pads 202 ECG via processor 208 to display 240 in the absence of a sensed connection to the monitoring electrodes 222.

In another exemplary embodiment of the present invention, also illustrated by FIG. 12, a defibrillator 200 processor 208 issues a shock advisory signal 228 to a high voltage circuit 230 if it determines that the analyzed cardiac rhythm is treatable by electrotherapy. Here, defibrillator 200 may be an ALS defibrillator operating in AED mode or an AED. If the defibrillator of this embodiment has a waveform display, it can display the waveform on display 240 as specified above. When both therapy pads 202 and limb lead monitoring electrodes 222 are attached to the patient, the defibrillator 200 senses the condition and automatically switches the source of ECG that is used by its automated shock advisory algorithm from the therapy pads 202 to the limb lead monitoring electrodes 222. This inventive practice is different from currently available defibrillators, which are known to exclusively use ECG from therapy pads as input to the shock advisory algorithm. Furthermore, if the defibrillator 200 is equipped with a CPR artifact reduction algorithm, the ECG can be filtered by that algorithm prior to use in the shock advisory algorithm.

Referring again to FIG. 12, illustrated is a block diagram of an exemplary embodiment of a defibrillator 200 that is constructed in accordance with an exemplary embodiment of the shock advisory in accordance with the present disclosure. The electrodes, connectors, ECG front end, and artifact detector circuits are essentially the same as previously described herein. In this embodiment, though, when defibrillator 200 senses that both a set of therapy pads 202 and limb lead monitoring electrodes 222 are attached to the patient, defibrillator 200 automatically switches the source of any shock advisory signal issued from processor 208 from the therapy pads to the limb lead electrodes for use as the shock advisory signal 228 input to the defibrillator high voltage shock delivery circuit 230. The shock delivery circuit 230 responsively arms and prepares a circuit to deliver a therapeutic shock to the patient via pads 202. Shock delivery may be semi-automatic or fully automatic as known in the defibrillation art.

If the defibrillator 200 is equipped with a CPR artifact reduction algorithm which also may have an input from artifact detector 210, processor 208 can filter the obtained ECG prior to analyzing the ECG for a shock advisory. The optional artifact noise detector 210 can, as previously described, develop an artifact level/decision that is provided to processor 208.

Processor 208 analyzes both ECG streams that it obtains from the therapy pads and the monitoring electrodes. Each ECG stream analysis results in a shock or no shock decision, as indicated by the two "S" outputs shown in FIG. 12. Processor 208 can further be disposed to filter one or both of the ECG streams prior to analysis for greater accuracy. Processor 208 can further use signals from artifact noise detector 210 as an input to the filtering function.

Defibrillator 200 can further include a sensing means for sensing when the monitoring electrodes have been attached to a patient, and for selecting the ECG stream from the monitoring electrodes for analysis in response to the sensed attachment. Several known methods for sensing the patient connection can be used, including, e.g., sensing a common mode signal between electrode connections at the monitoring electrode connector, sensing an ECG signal at the ECG front end 226, sensing a patient-appropriate impedance between electrodes, all of which can be supplemented with a sensing of the electrode hardware to the monitoring electrodes connector 224 itself. In a preferred embodiment, the sensing means is disposed as controller 216 and a control switch 217 in a hardware circuit. A functionally equivalent sensing means can also be embodied in software with a microprocessor and memory, or as a software/hardware state machine system.

In a preferred embodiment, controller 216 receives a signal from electrodes ECG front end 226 which indicates that the set of monitoring electrodes 222 is connected to the patient via the monitoring electrodes connector 224. In response to the sensed connection, connector 216 controls controller switch 217 to automatically switch a shock advisory source, signified by the "S" inputs from processor 208, to the monitoring electrodes source. The shock advisory signal resulting from the monitoring electrodes 222 ECG is thus provided as a shock advisory signal 228 to shock delivery circuit 230.

Controller 216 can optionally receive input from artifact noise detector 210. If the detected level of noise artifact is below a predetermined noise level, then controller 216 may drive controller switch 217 to toggle the shock advisory source back to the therapy pads source. This option can be desirable in situations where the therapy pads shock advisory algorithm is more accurate than the monitoring electrodes shock advisory algorithm, and provides more analyses that are in accordance with the current practice of determining electrotherapy from the same source as through which it is delivered.

It will be appreciated by one having ordinary skill in the art in view of the teachings provided herein that the predetermined noise level for shock advisory can be different than that for a display decision. The proper predetermined noise level can be determined by one having ordinary skill in the art in view of the teachings provided herein by conducting a series of trial and error experiments that have varying amounts of known noise and ECG signal levels present. Simulated ECG signal data can be fed into the system under various conditions of noise artifact presence, including CPR-related artifact. This and other methods of finding such heuristic values should be known to one having ordinary skill in the art.

It is also to be noted that in the absence of the monitoring electrodes, the nominal source of shock advice in defibrillator 200 is generally the same as that of existing defibrillators, eg., the therapy pads 202 ECG. Consequently, controller 216 controls controller switch 217 to route the therapy pads 202 ECG via processor 208 to display 240 in the absence of a sensed connection to the monitoring electrodes 222.

According to exemplary embodiments of the present disclosure, the use of lead electrode ECG for display and shock advisory can be a user-configurable option on the defibrillator. For example, this option can be configured during set-up of the defibrillator, or it can be turned "ON" or "OFF" during the resuscitation by press of a button, not shown.

Figure 13:
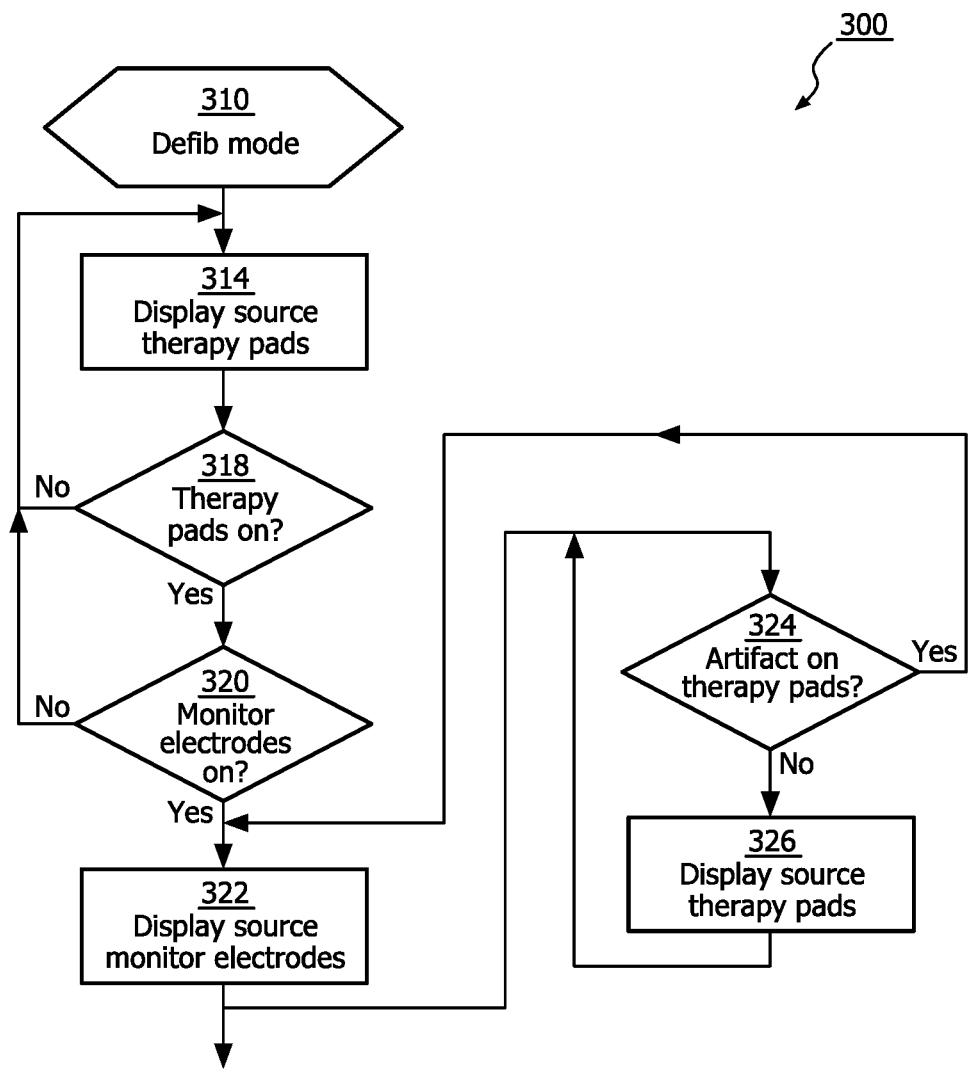
FIG. 13 is an exemplary illustration of a process flow diagram according to one embodiment of the inventive method, showing the method of determining the display source of the ECG.

FIG. 13 illustrates a process flow diagram according to an exemplary embodiment of the present invention, showing, for example, a method of determining the display source of the ECG 300. The exemplary method initiates by providing a defibrillator in defibrillation mode at step 310, the defibrillator disposed similarly to that described previously, e.g., having a therapy pads connector, a monitoring electrodes connector, a processor operable to obtain an electrocardiogram (ECG) responsive to inputs from either of the therapy pads connector and the monitoring electrodes connector, and a controller operable to sense a connection of therapy pads to the therapy pads connector and operable to sense a connection of monitoring electrodes to the monitoring electrodes connector.

For example, at the beginning of the cardiac rescue event, the defibrillator is activated by the user. At this time, the defibrillator begins operation, and in most cases the display source defaults to the therapy pads ECG obtained via the therapy electrodes connector at step 314. The default display serves to initially guide the rescuer as to placement of the therapy pads for as rapid a delivery of needed electrotherapy as possible. A pad placement loop then begins at step 318 of sensing the connection of the therapy pads. As long as the therapy pads remain unconnected, the defibrillator continues to provide aural and visual guidance to the operator to connect them. In those rescues in which defibrillation is clearly not needed, the user can override the pad placement loop, and exit the method altogether.

When therapy pads are detected as connected and on the patient, the method proceeds to step 320, sensing the connection of the monitoring electrodes. Another guidance loop can be entered in this step, allowing the defibrillator to prompt the user to place the monitoring electrodes on the subject patient. When so accomplished, patient ECG signals are being received by both of the therapy pads and the monitoring electrodes. Responsive to step 320, the display is automatically switched from the default therapy pads source of ECG signals to the monitoring electrodes ECG signals at step 322. In this state, both pads and electrodes are connected, and the ECG displayed on the defibrillator is the monitoring electrodes source of ECG which presumably has the lower level of CPR-related noise artifact. In order to further reduce the level of noise artifact, a filtering step can be performed on the monitoring electrodes ECG prior to the displaying step.

FIG. 13 also illustrates an optional step of analyzing the therapy pads ECG for artifact, including CPR-related noise, at step 324. Step 324 is repeated in a looping function as long as any ECG is displayed. During those periods of time in which the therapy pads ECG is determined to be noise-free, then the display source toggles back to the therapy pads ECG. This option can be desirable, e.g., for some users that prefer to display ECG from therapy pads whenever possible and useful, or in situations where the therapy pads ECG display is more accurate or easier to interpret than the monitoring electrodes display.

Figure 14:
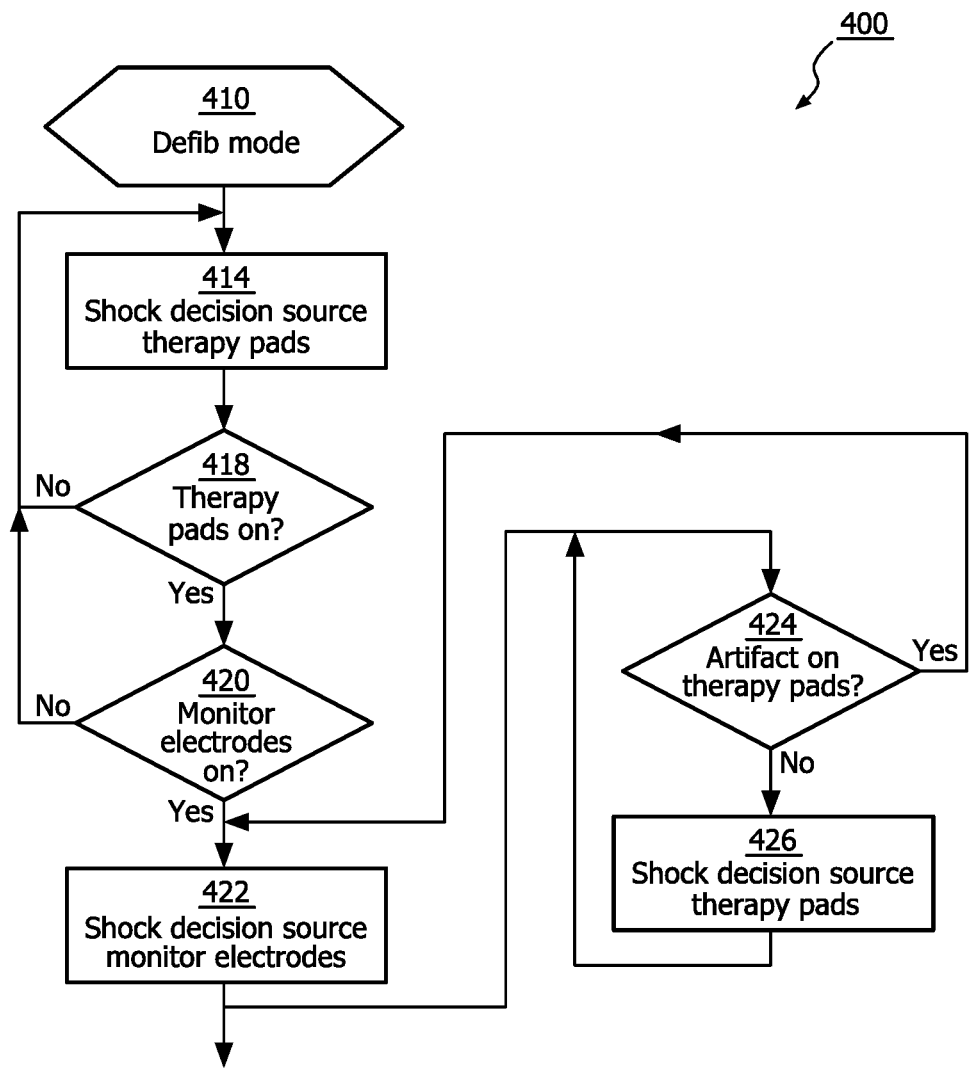
FIG. 14 is an exemplary illustration of a process flow diagram according to one embodiment of the inventive method, showing the method of determining shock analysis source for the defibrillator.

FIG. 14 illustrates a process flow diagram according to another embodiment of the inventive method, showing a method of operating a defibrillator during a cardiac resuscitation 400, and more specifically for selecting an optimal shock analysis source. The method initiates by providing a defibrillator in defibrillation mode at step 310, the defibrillator disposed similarly to that described previously, e.g., having a therapy pads connector, a monitoring electrodes connector, a processor operable to analyze the obtained ECG to determine whether electrotherapy is indicated responsive to inputs from either of the therapy pads connector and the monitoring electrodes connector, and a controller operable to sense a connection of therapy pads to the therapy pads connector and operable to sense a connection of monitoring electrodes to the monitoring electrodes connector.

At the beginning of the cardiac rescue event, the defibrillator is activated by the user. At this time, the defibrillator begins operation, and in most cases the shock analysis source defaults to the therapy pads ECG obtained via the therapy electrodes connector at step 414. As before, a pad placement loop begins at step 418 of sensing the connection of the therapy pads, which allows the defibrillator to automatically guide the rescuer as to placement of the therapy pads for as rapid a delivery of needed electrotherapy as possible. As long as the therapy pads remain unconnected, the defibrillator continues to provide aural and visual guidance to the operator to connect them. In those rescues in which defibrillation is clearly not needed, the user can override the pad placement loop, and exit the method altogether.

When therapy pads are detected as connected and on the subject patient, analysis begins on the ECG from the therapy pads via the therapy electrodes connector. While analysis is occurring, the method proceeds to step 420, sensing the connection of the monitoring electrodes. Another guidance loop can be entered in this step, allowing the defibrillator to prompt the user to place the monitoring electrodes on the subject patient. When so accomplished, analysis begins on the patient ECG signals being received by the monitoring electrodes as well. In this state, ECG in both of the therapy pads and the monitoring electrodes are being analyzed for the advisement of electrotherapy. But responsive to step 420, the shock decision source is automatically switched from the default therapy pads source of ECG signals to the monitoring electrodes ECG signals at step 422. In this state, both pads and electrodes are connected, and the shock advisory source signal being provided to the defibrillator's shock delivery circuit is from the monitoring electrodes source of ECG, presumably the source having has the lower level of CPR-related noise artifact. In order to further reduce the level of noise artifact, a filtering step may be performed on the monitoring electrodes ECG prior to the analyzing step.

FIG. 14 also illustrates an optional step, in accordance with exemplary embodiments of the present invention, of analyzing the therapy pads ECG for artifact, including for CPR-related noise, at step 424. Step 424 is repeated in a looping function as long as any shock analysis is occurring. During those periods of time in which the therapy pads ECG is determined to be noise-free, then the shock advisory source toggles back to the therapy pads ECG. This option can be desirable for some users that prefer to use ECG from therapy pads because of local operating protocol, or in situations where the therapy pads ECG shock advisory algorithm is more accurate than the monitoring electrodes algorithm, for example.

One having ordinary skill in the art should appreciate that modifications to the exemplary device, system and method as herein are encompassed within the scope of the present invention. For example, references here to "limb lead electrodes" or "electrode lead" ECG may include ECG from any of the standard limb leads I, II, III, aVR, aVL, aVF. Although in practice leads V1, V2, V3, V4, V5, or V6, or any other precordial or right sided ECG lead would likely be less optimal for use in the inventive apparatus and methods due to their proximity to the site of CPR compressions (sternum), the invention is not limited by excluding the possible use of these leads.

Furthermore, the placement of the limb lead electrodes may be either on the Mason-Likar (on torso) locations used routinely for continuous ECG monitoring (Left and Right Arm electrodes on shoulders or clavicles; leg electrodes on lower abdomen), or positioned in the standard 12-lead diagnostic locations of wrists and ankles.

A further embodiment can allow display of both ECG from therapy pads and ECG monitoring leads simultaneously (in different waveform areas of the device's display). In this embodiment, any ECG waveform may be labeled appropriately as "PADS" or "LEAD X" (where X corresponds to the user selected standard limb leads such as I, II, III, aVR, AVL, aVF).

Further, as one having ordinary skill in the art will appreciate in view of the teachings provided herein, features, elements, components, etc. described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figure can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read-only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments for systems, devices, and methods for monitoring a subject cardiac rhythm during the application of cardio-pulmonary resuscitation (CPR) (which embodiments are intended to be illustrative and not limiting), it is noted that modifications and variations can be made by persons skilled in the art in light of the teachings provided herein (including the appended Figures). It is therefore to be understood that changes can be made in/to the preferred and exemplary embodiments of the present disclosure which are within the scope of the embodiments disclosed herein.

What is claimed is:

1. A method for selectively displaying an ECG on a defibrillator during a cardiac resuscitation of a subject, comprising the steps of:
    providing a defibrillator having a display, a therapy pads connector, a monitoring electrodes connector separate from the therapy pads connector, a processor operable to obtain an electrocardiogram (ECG) responsive to inputs from both of (i) the therapy pads connector and (ii) the monitoring electrodes connector, and a controller operable to sense both (a) a connection of therapy pads to the therapy pads connector and (b) a connection of monitoring electrodes to the monitoring electrodes connector;
    displaying, initially, an ECG obtained from a source that comprises the therapy pads connector; and
    automatically switching the source of the displaying of the ECG obtained from the therapy electrodes connector to a source of displaying of an ECG obtained from the monitoring electrodes connector responsive to sensing both (i) a connection of a set of therapy pads to the therapy pads connector and (ii) a connection of a set of monitoring electrodes to the monitoring electrodes connector.

2. The method of claim 1, further comprising a filtering step of filtering the ECG from the monitoring electrodes prior to the displaying step.

3. The method of claim 1, further comprising a step of toggling a source of the displaying back to the ECG obtained from the therapy electrodes connector subsequent to the automatically switching step.

4. The method of claim 3, wherein the toggling step is automatic based on a sensed noise-free ECG obtained from the therapy electrodes connector.

5. The method of claim 4 further comprising:
    analyzing the ECG obtained from the therapy electrodes connector; and
    automatically switching the analyzing of the ECG obtained from the therapy electrodes connector to an analyzing of the ECG obtained from the monitoring electrodes connector responsive to the sensing step.

6. The method of claim 5, further comprising a filtering step of filtering the ECG from the monitoring electrodes prior to the analyzing step.

7. The method of claim 5, further comprising a step of toggling the analyzing back to the ECG obtained from the therapy electrodes connector subsequent to the automatically switching step, wherein the toggling step is automatic based on a sensed noise-free ECG obtained from the therapy electrodes connector.

8. A defibrillator comprising:
    a therapy pads connector operable to connect to a set of therapy pads;
    a monitoring electrode connector separate from the therapy pads connector and operable to connect to a set of monitoring electrodes;
    a processor operable to obtain an ECG from both of (i) the therapy pads and (ii) the monitoring electrodes;
    a sensor operable to sense both (i) the connection of the set of therapy pads to the therapy pads connector and (ii) the connection of the set of monitoring electrodes to the monitoring electrode connector, and further operable to automatically select the ECG obtained from the monitoring electrodes, instead of the ECG obtained from the therapy pads, for display in response to the sensed connection of both (i) the connection of the set of therapy pads to the therapy pads connector and (ii) the connection of the set of monitoring electrodes to the monitoring electrode connector; and
    a display operable to display the selected ECG.

9. The defibrillator of claim 8, wherein the processor is operable to filter the obtained ECG for removing noise artifact.

10. The defibrillator of claim 8, wherein the sensor comprises a controller.

11. The defibrillator of claim 10, wherein the sensor is further operable to automatically select the ECG obtained from the therapy pads in an absence of a sensed connection of the set of monitoring electrodes to the monitoring electrode connector.

12. The defibrillator of claim 8, wherein the monitoring electrodes are operable to be disposed on a patient in a standard limb lead orientation.

13. The defibrillator of claim 8, further comprising:
    an artifact detector operable to determine the level of noise artifact on the ECG obtained from the therapy pads,
    wherein the sensor is further operable to toggle a source of the ECG for display from the ECG obtained from the monitoring electrodes to the ECG obtained from the therapy pads if the level of noise artifact is below a predetermined noise level.

14. The defibrillator of claim 8, further comprising:
    a high voltage shock delivery circuit;
    wherein the processor is further operable to analyze the ECG obtained from either of the therapy pads or the monitoring electrodes, and to determine a shock decision based on the obtained ECG;
    wherein the sensor is further to automatically select a shock decision based on the ECG obtained from the monitoring electrodes in response to the sensed connection; and
    wherein the high voltage shock delivery circuit is operable to deliver an electrotherapy shock via the therapy pads connector and therapy pads in response to the shock decision based on the ECG obtained from the monitoring electrodes.

15. The defibrillator of claim 14,
    wherein the sensor is further operable to automatically select a shock decision based on the ECG obtained from the therapy pads in the absence of a sensed connection of the set of monitoring electrodes to the monitoring electrode connector; and
    wherein the high voltage shock delivery circuit is further operable to deliver the electrotherapy shock via the therapy pads connector and the therapy pads in response to the shock decision based on the ECG obtained from the therapy pads.

* * * * *